(12) United States Patent
Pagan

(10) Patent No.: US 6,261,401 B1
(45) Date of Patent: Jul. 17, 2001

(54) LARYNGEAL MASKS AND MANUFACTURE

(75) Inventor: Eric Pagan, Hythe (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 09/303,540

(22) Filed: May 3, 1999

(30) Foreign Application Priority Data

May 9, 1998 (GB) .................................................. 9809897

(51) Int. Cl.$^7$ .................................................. A61M 16/00
(52) U.S. Cl. ..................... 156/182; 156/199; 156/267; 156/269; 156/292; 128/207.14
(58) Field of Search ..................... 156/292, 199, 156/209, 250, 269, 267, 510, 522, 526, 528, 182; 128/207.15, 207.14

(56) References Cited

U.S. PATENT DOCUMENTS

| 4,415,398 | 11/1983 | Ottaviano . |
| 5,305,743 | 4/1994 | Brain . |
| 5,355,879 | * 10/1994 | Brain ................................ 128/207.15 |
| 5,794,617 | 8/1998 | Brunnell et al. . |
| 5,997,676 | * 12/1999 | Jurrius et al. ......................... 156/228 |

* cited by examiner

Primary Examiner—Michael W. Ball
Assistant Examiner—Barbara J. Musser
(74) Attorney, Agent, or Firm—Connolly Bove Lodge & Hutz, LLP

(57) ABSTRACT

Mask formations of a laryngeal mask airway are made from two tracks of sheet plastics material. Each sheet track comprises two layers sandwiching ring-shape reinforcements between them. A station along each track pressure-vacuum forms the regions of the reinforcements into cuff members. The two tracks come together and the cuff members are joined to opposite sides of mount members to complete the mask formations.

7 Claims, 2 Drawing Sheets

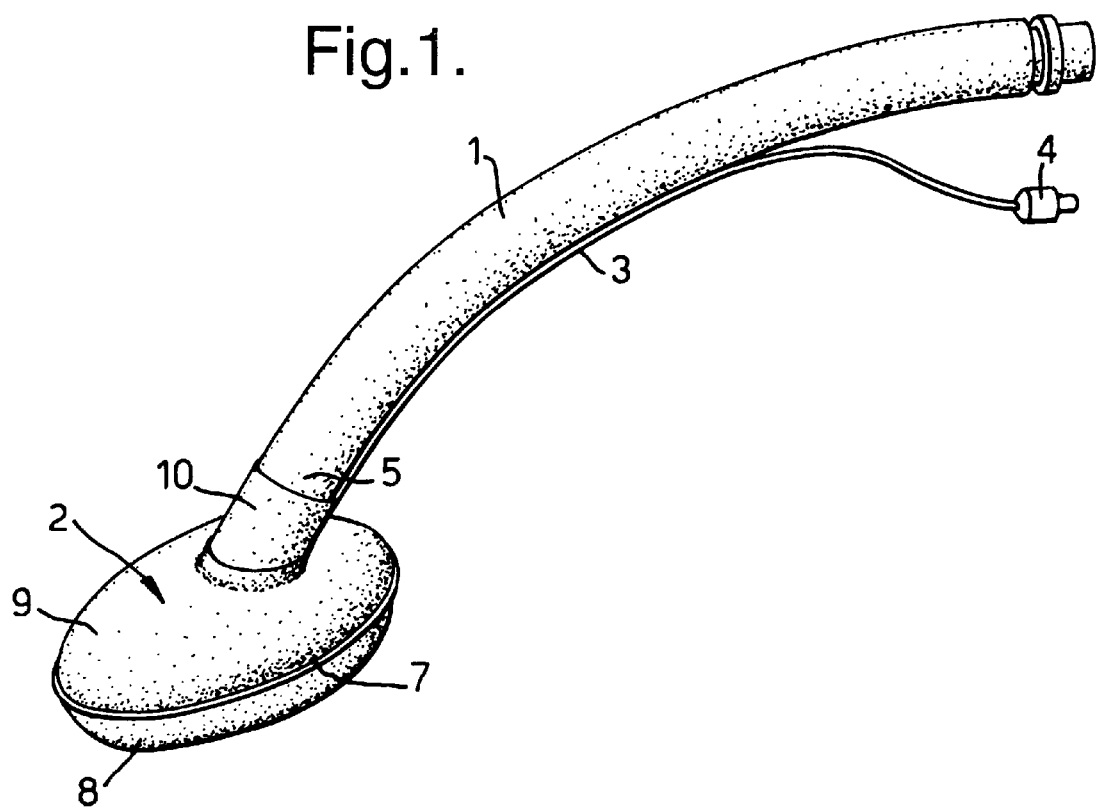
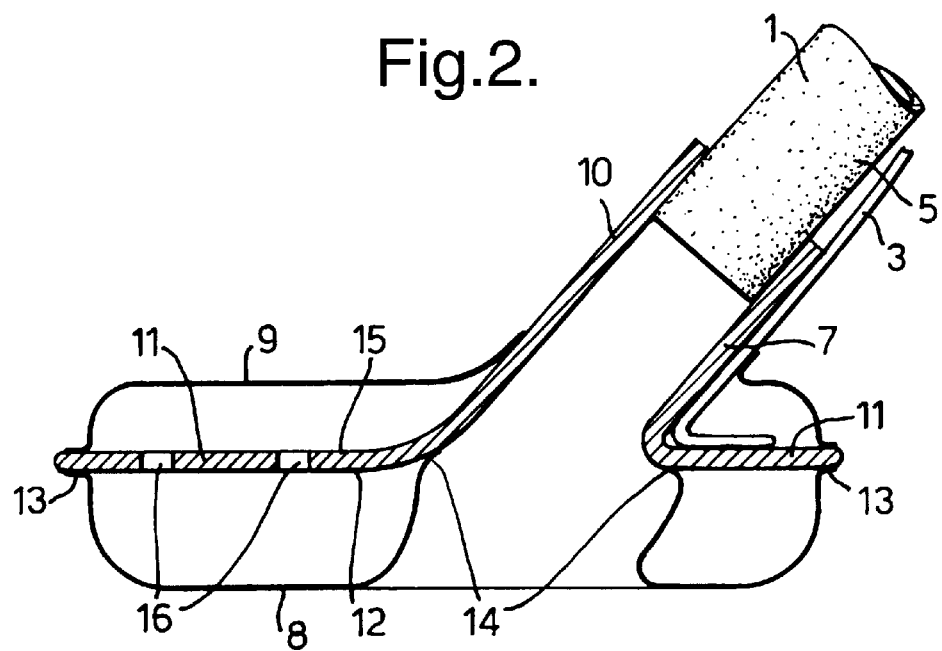

LARYNGEAL MASKS AND MANUFACTURE

BACKGROUND OF THE INVENTION

This invention relates to laryngeal masks and their manufacture.

Laryngeal mask airways are used to ventilate and provide anaesthetic gas to a patient during surgery. Laryngeal mask airways differ from endotracheal tubes, which extend into the trachea and terminate beyond the vocal folds. By contrast, laryngeal mask airways have a tube opening into the centre of a generally elliptical mask, which seals in the region of the hypopharynx, at the top of the trachea. Laryngeal masks are described in, for example, U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2317830, GB 2249959, GB 2111394, EP 448878, U.S. Pat. No. 4,995,388, GB 2205499, GB 2128561, GB 2298797, GB 2321854, GB 9900596, GB 2323289, GB 2323290, GB 2318735 and GB 2330312. Laryngeal mask airways have certain advantages over endotracheal tubes but their more complex construction makes them considerably more expensive. As a result, the majority of laryngeal mask airways are reusable devices, which are sterilized after use.

BRIEF SUMMARY OF THE INVENTION

It is an object of the present invention to provide an improved method of manufacture of laryngeal mask airways, and airways made by this method.

According to one aspect of the present invention there is provided a method of making a mask formation for a laryngeal mask airway comprising the steps of moving two sheets of plastics material along their length, moulding from the sheets components of a mask formation for the airway, bringing the sheets towards one another and joining components on the two sheets to form the mask formation for the airway, and separating the mask formation from the sheets.

The first sheet preferably includes a reinforcement member, which may be of ring-shape, sandwiched between two layers of sheet material. The second sheet preferably includes a reinforcement member, which may be of ring-shape, sandwiched between two layers of sheet material. The reinforcement member may be sandwiched between the layers of sheet material by peeling the reinforcement member off a supply sheet. The components of the sheets are preferably joined with opposite sides of a mount member to provide a cuff member on opposite sides of the mask formation. The components may be moulded by a pressure-vacuum process.

According to another aspect of the present invention there is provided a mask formation made by a method according to the above one aspect of the invention.

According to a further aspect of the present invention there is provided a machine for use in a method according to the above one aspect of the invention.

According to a fourth aspect of the present invention there is provided a machine for making a mask formation for a laryngeal mask airway comprising a first and second track of sheet plastic material arranged to move together towards one end, a first forming station intermediate the ends of the first track for moulding a first cuff component from the sheet in the first track, a second forming station intermediate the ends of the second track for moulding a second cuff component from the sheet in the second track, and a third station for joining the first and second cuff components to opposite sides of a mount member to form the mask formation.

According to a fifth aspect of the present invention there is provided a mask made on a machine according to the above fourth aspect of the invention.

A machine and method for making a mask for a laryngeal mask airway and a mask made by the method, according to the present invention, will now be described, by way of example, with reference to the accompanying drawings.

BRIEF DESCRIPTION OF THE DRAWINGS

FIG. 1 is a perspective view of a laryngeal mask airway;

FIG. 2 is a cross-sectional side elevation of the patient end of the airway.

DETAILED DESCRIPTION OF THE PREFERRED EMBODIMENT

Figure 3:
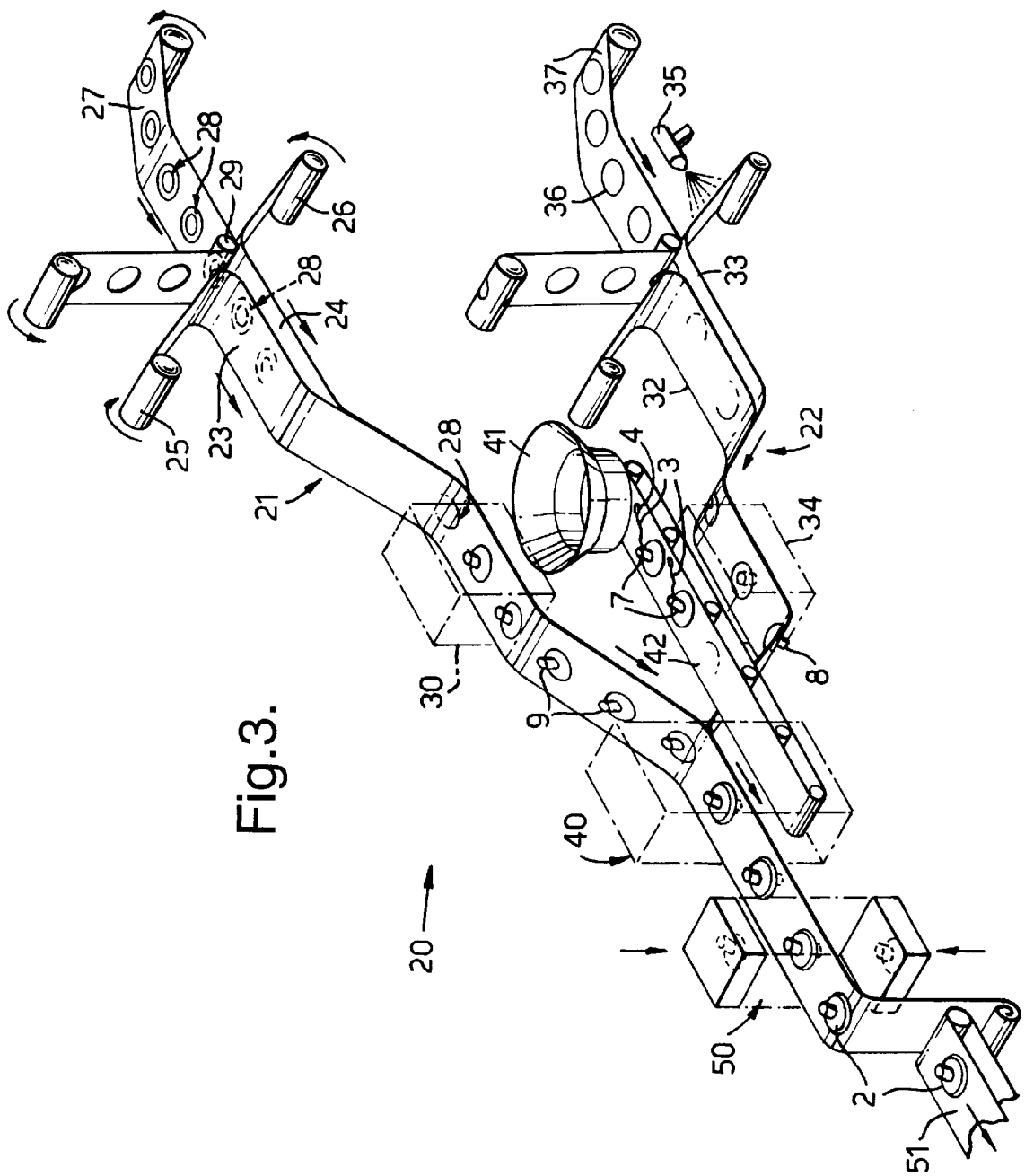
FIG. 3 illustrates the manufacture of the mask assembly of the airway.

With reference first to FIGS. 1 and 2, the airway comprises an extruded, curved tube 1 with a mask assembly or formation 2 at its patient end. An inflation line 3 extends along the length of the tube 1 and is terminated at its machine end with an inflation indicator balloon and connector 4.

The mask assembly 2 comprises a relatively rigid mount member 7 and two inflatable cuffs 8 and 9 on opposite sides of the mount member. The mount member 7 has a tubular portion 10 within which the patient end 5 of the tube 1 is bonded, and an integral plate member 11 of elliptical shape projecting outwardly at an angle of about 30 degrees to the axis of the tubular portion 10 so that the tubular portion opens in a central part of the plate member. One cuff 8 takes the form of a thin, flexible ring-shape sheet of plastics material bonded to the patient side 12 of the plate member 11 around its outer edge 13 and inner edge 14. The other cuff 9 is a similar ring-shape sheet of plastics material bonded to the opposite side 15 of the plate member 11 and to the outside of the tubular portion 10. The patient end of the inflation line 3 extends between the plate member 11 and the rear cuff 9, at one side. Apertures 16 through the plate member 11 enable gas to flow between the two cuffs 8 and 9. In this way, the cuffs 8 and 9 can be inflated away from the plate member 11 to form a resilient annular cushion around both sides of the patient end of the assembly, by supplying air, or other inflation fluid via the inflation line 3. The inflated cuffs 8 and 9 provide a conformable seal at the patient end of the assembly with the patient tissue in the region of the hypopharynx so that the tube opens into the top of the trachea and is sealed from the oesophagus, in the usual way.

With reference to FIG. 3, the machine and method by which the mask assembly 2 is formed will now be described. The method involves the use of a machine in the form of an assembly line indicated generally by the numeral 20, which has two separate tracks of sheet 21 and 22, running from right to left, which come together to join different components of the mask assembly 2. The upper track 21 has two layers 23 and 24 of sheet plastics material supplied off respective rolls 25 and 26. One or both the sheets 23 and 24 may be coated with an adhesive on the surface facing the other sheet. A third, supply sheet 27 is die cut with ring-shape, planar reinforcing members 28, which peel off the sheet where it bends around a guide roller 29 adjacent the upper surface of the lower sheet 24, so that the reinforcing members are sandwiched between the two sheets 23 and 24 and are transported to the first forming station 30.

At the first forming station 30, the region of the reinforcing planar members 28 and the regions of the two sheets 23 and 24 in which the members are trapped are subject to a pressure-vacuum forming operation. This has the effect of bonding the two sheets intimately with one another and with the reinforcing member, and of moulding the combined laminate structure to form the rear cuff member 9. The reinforcement members 28 are used to strengthen certain parts of the cuff 9 so that it inflates preferentially in the unreinforced regions, thereby producing the desired shape, which can be more intricate than with unreinforced cuffs.

The lower track 22 provides the forward cuff member 8 and has two layers of sheet material 32 and 33, which move from right to left to a lower forming station 34. One or both sheets 32 and 33 may have an adhesive coating, such as provided by a spray gun 35. The two sheets 32 and 33 may also trap between them a thin, planar, ring-shape reinforcing member 36 fed from a separate supply roll 37. At the lower forming station 34, the laminate sheet arrangement of the two layers 32 and 33, with the optional reinforcing member 36, are pressure-vacuum formed to the desired shape. In the present example the shape produced is the desired shape of the uninflated cuff 8, that is, an elliptical ring with a concave channel extending around its upper surface. The inflated shape of the cuff 8 can be slightly different from its uninflated shape because the reinforcing members 36 allow preferential inflation in the unreinforced regions.

After passing through the lower forming station 34, the two tracks 21 and 22 come together at a third station 40. The third station 40 has a supply hopper 41 of the rigid mount members 7 attached with the inflation lines 3 and their inflation indicators and connectors 4. These are conveyed along a short belt 42 extending alongside the two tracks 21 and 22. The third station 40 positions the mount members 7 between the formed cuff members 9 and 8 on the upper and lower tracks 21 and 22, so that the mount members are located between the two cuff members.

The upper and lower tracks 21 and 22 now proceed together to a fourth station 50, where the members on the upper and lower sheets are joined to the mount members 7 and cut out from their respective sheets. This may be done by a push-fit arrangement, by welding, by a cut-punch arrangement or by a combination of any of these. The completed mask assemblies 2 are then ejected onto another conveyor belt 51 where they are carried to a subsequent station (not shown) for assembly onto the tube 1 in a conventional manner.

The cuffs 8 and 9 could be filled with a foam material so that they have a naturally inflated state and are sucked down to deflate it for insertion or removal. The foam could be added by injecting a liquid foam material into the cuff after attachment to the mount member, or by positioning a preformed foam sheet between the cuff and the mount member prior to joining these two components.

The present invention enables considerable automation in the manufacture of a laryngeal mask assembly.

The arrangement described above can be readily modified to form different arrangements of laryngeal mask assembly.

What I claim is:

1. A method of making a mask formation for a laryngeal mask airway comprising the steps of:

moving a first sheet and a second sheet of plastics material along their length wherein said first sheet includes two layers of sheet material and a ring-shaped reinforcement member sandwiched between said two layers;

moulding from said sheets components of a mask formation for said airway;

bringing said sheets towards one another;

joining components on said two sheets with one another to form said mask formation for said airway; and separating said mask formation from said sheets.

2. A method according to claim 1, wherein said reinforcement member is sandwiched between the layers of sheet material by peeling the reinforcement member off a supply sheet.

3. A method according to claim 1, wherein said second sheet includes two layers of sheet material and a reinforcement member sandwiched between said two layers.

4. A method according to claim 3, wherein said reinforcement member of said second sheet is of ring shape.

5. A method according to claim 1, wherein said components are moulded by a pressure-vacuum process.

6. A method according to claim 1, wherein said components of said sheets are joined with opposite sides of a mount member to provide cuff members on opposite sides of said mask formation.

7. A method of making a mask formation for a laryngeal mask airway comprising the steps of: sandwiching between two layers of sheet material a series of first reinforcement members of ring shape to form a first sheet track; moulding first cuff components from said first sheet track in a region of said first reinforcement members; sandwiching between two layers of sheet material a series of second reinforcement members of ring shape to form a second sheet track; moulding second cuff components from said second sheet track in a region of said second reinforcement members; and joining said first and second cuff components to opposite sides of a mount member to form said mask formations for said airway.

* * * * *